(12) United States Patent
Thornbury et al.

(10) Patent No.: US 7,131,965 B1
(45) Date of Patent: Nov. 7, 2006

(54) MEDICAL FLUID COLLECTION AND REMOVAL DEVICE

(75) Inventors: Thomas R. Thornbury, Chatsworth, CA (US); Pradip V. Choksi, Chatsworth, CA (US); Julie A. Ryan, Hoover, AL (US)

(73) Assignee: Hemotrans, Inc., Valencia, CA (US)

( * ) Notice: Subject to any disclaimer, the term of this patent is extended or adjusted under 35 U.S.C. 154(b) by 396 days.

(21) Appl. No.: 10/206,293

(22) Filed: Jul. 25, 2002

Related U.S. Application Data

(60) Provisional application No. 60/341,501, filed on Dec. 20, 2001.

(51) Int. Cl.
*A61B 19/00* (2006.01)
*A61M 27/00* (2006.01)
*A47K 3/02* (2006.01)

(52) U.S. Cl. ............... 604/356; 604/541; 4/581; 211/132.2; 137/312; 141/86

(58) Field of Classification Search ........ 604/540, 604/541, 317, 356; 4/679, 581–583; D24/108; 269/15; 312/229; 211/132.1; 137/312; 5/606; 141/86; 184/106
See application file for complete search history.

(56) References Cited

U.S. PATENT DOCUMENTS

| | | | | |
|---|---|---|---|---|
| 868,137 | A * | 10/1907 | Shriver | 604/356 |
| 2,503,174 | A * | 4/1950 | Salvadore | 4/661 |
| 2,650,855 | A * | 9/1953 | Peirce | 296/97.23 |
| 3,082,032 | A * | 3/1963 | Stata | 296/97.23 |
| 3,696,459 | A * | 10/1972 | Kucera et al. | 15/104.92 |
| 3,757,356 | A * | 9/1973 | Freeman | 4/456 |
| 3,763,857 | A * | 10/1973 | Schrading | 128/853 |
| 3,783,863 | A * | 1/1974 | Kliever | 128/847 |
| 4,243,214 | A * | 1/1981 | LaRooka | 5/630 |
| 4,260,311 | A * | 4/1981 | Hanses | 414/795.6 |
| 4,525,166 | A * | 6/1985 | Leclerc | 604/133 |
| 4,533,352 | A * | 8/1985 | Van Beek et al. | 604/317 |
| 4,635,913 | A * | 1/1987 | Rothman | 5/658 |
| 4,679,590 | A | 7/1987 | Hergenroeder | |
| 4,718,653 | A * | 1/1988 | Rothman | 5/658 |
| 4,729,404 | A | 3/1988 | Hergenroeder | |
| 4,811,937 | A * | 3/1989 | Rothman | 5/606 |
| 4,889,155 | A * | 12/1989 | Trotter, Sr. | 137/312 |
| 4,936,456 | A * | 6/1990 | Bell et al. | 206/439 |
| 5,020,638 | A * | 6/1991 | Smith | 184/106 |
| 5,176,667 | A * | 1/1993 | DeBring | 604/356 |
| 5,233,735 | A * | 8/1993 | Haley | 27/21.1 |
| 5,255,404 | A * | 10/1993 | Dinsmoor et al. | 5/677 |
| 5,349,965 | A * | 9/1994 | McCarver | 128/846 |
| 5,437,651 | A * | 8/1995 | Todd et al. | 604/313 |
| 5,547,312 | A * | 8/1996 | Schmitz, Jr. | 405/52 |
| 5,552,169 | A * | 9/1996 | Kannankeril et al. | 426/107 |
| 5,628,735 | A | 5/1997 | Skow | |
| 5,675,854 | A * | 10/1997 | Zibelin | 5/695 |
| 5,720,078 | A * | 2/1998 | Heintz | 15/415.1 |
| 5,738,139 | A * | 4/1998 | DeChard | 137/312 |
| 5,775,869 | A * | 7/1998 | Bishop | 414/608 |
| 5,827,246 | A | 10/1998 | Bowen | |
| 5,836,309 | A | 11/1998 | Webb | |

(Continued)

*Primary Examiner*—Tatyana Zalukaeva
*Assistant Examiner*—Michael G. Bogart
(74) *Attorney, Agent, or Firm*—William W. Haefliger

(57) ABSTRACT

Liquid collection apparatus usable during surgery, comprising a shallow tray defining a liquid receiving zone that is upwardly exposed for receiving liquid dropping from a surgery area, and a liquid collector in a zone for collecting dropping liquid while allowing a surgeon to tread over a collector, during surgery.

35 Claims, 3 Drawing Sheets

U.S. PATENT DOCUMENTS

| | | |
|---|---|---|
| 5,906,025 A | 5/1999 | Johnson |
| D414,972 S * | 10/1999 | Williams ..................... D6/582 |
| 6,102,073 A * | 8/2000 | Williams ..................... 137/602 |
| 6,136,098 A | 10/2000 | Tribastone |
| 6,223,894 B1 * | 5/2001 | Lemaire ..................... 206/204 |
| 6,290,685 B1 * | 9/2001 | Insley et al. ................. 604/317 |
| 6,531,206 B1 * | 3/2003 | Johnston et al. ............ 428/172 |
| 6,568,419 B1 * | 5/2003 | Robinson et al. ............ 137/312 |
| 6,578,520 B1 * | 6/2003 | Otsuji et al. ................. 119/165 |
| D480,805 S * | 10/2003 | Thornbury et al. ......... D24/108 |
| 6,637,453 B1 * | 10/2003 | Robinson .................... 137/312 |
| 6,802,281 B1 * | 10/2004 | Otsuji et al. ................. 119/169 |
| 6,938,639 B1 * | 9/2005 | Robinson .................... 137/312 |
| 2003/0068463 A1 * | 4/2003 | Polley .......................... 428/71 |

* cited by examiner

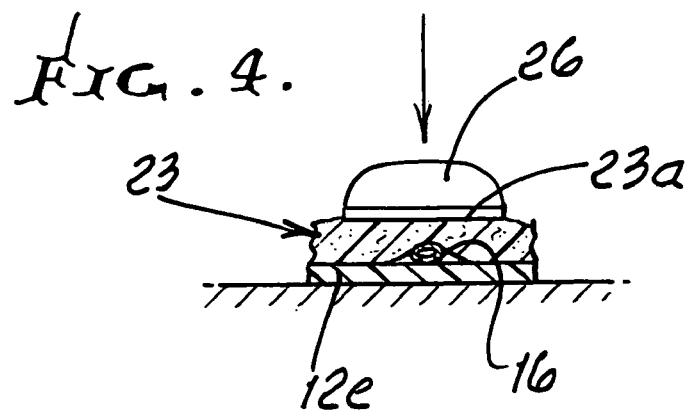
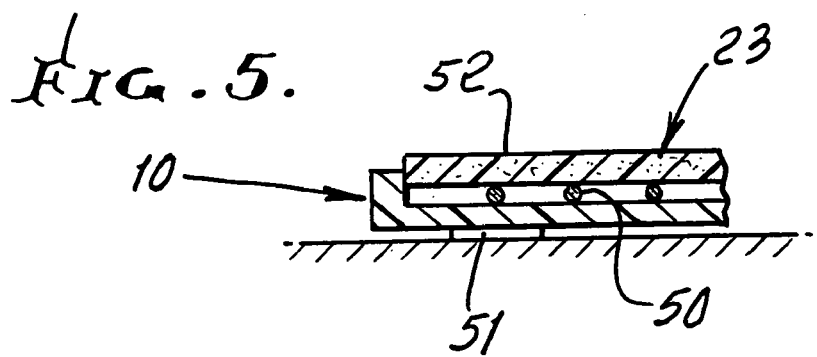
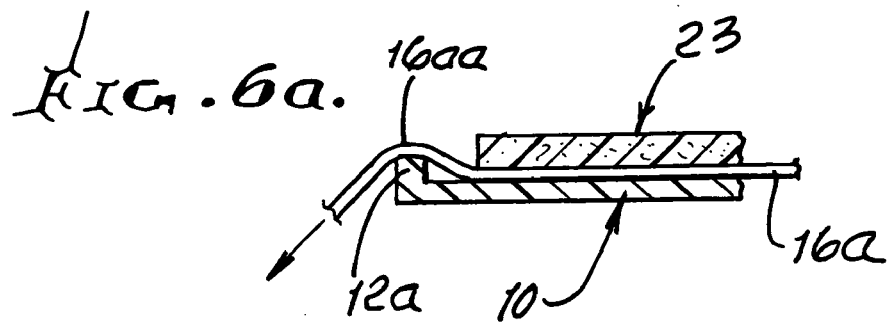
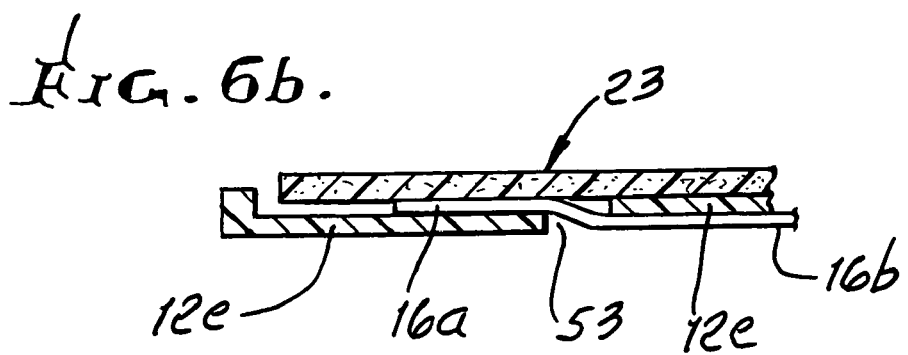

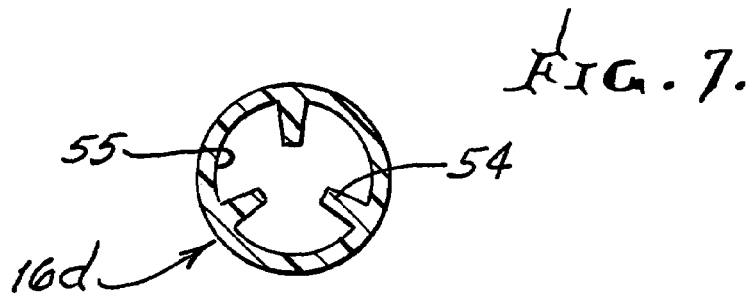
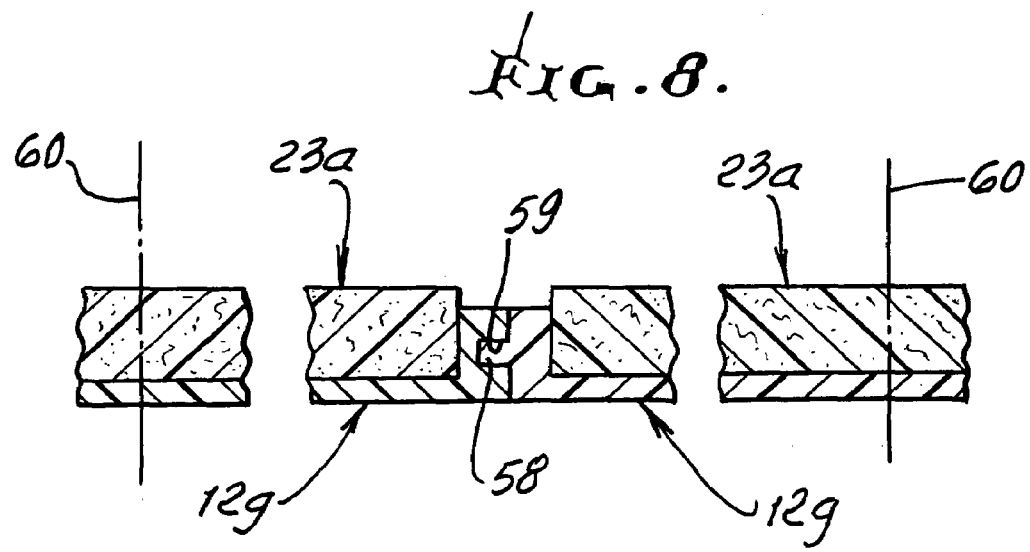
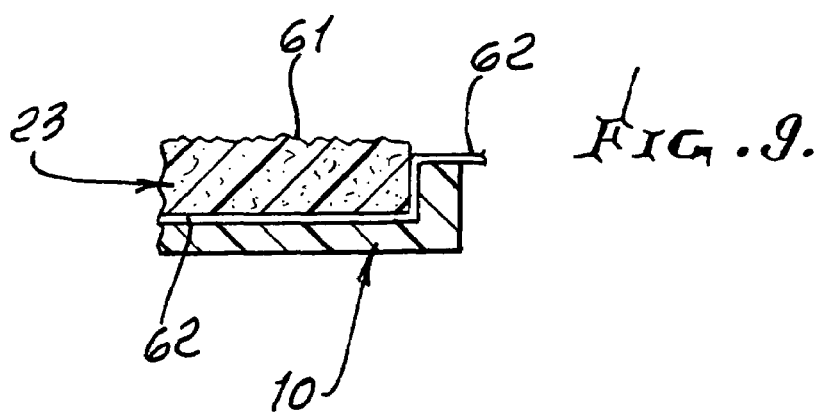

MEDICAL FLUID COLLECTION AND REMOVAL DEVICE

This application claims priority over provisional application Ser. No. 60/341,501, filed Dec. 20, 2001.

BACKGROUND OF THE INVENTION

This invention relates generally to liquid collection apparatus usable during surgery to collect liquid drainage from the surgery area; and more particularly concerns an easily manipulated liquid collection tray and liquid collector in the tray allowing surgeon treading over the collector.

During surgery, liquid such as sterile water supplied or used as irrigation liquid is commonly allowed to drain to the floor and collects there. This increases floor slipperiness and interferes with surgical procedures. There is need for improvements in such collection and disposal methods, as well as ease of handling and manipulation of collection and disposal apparatus, as well as ease of rolling travel of operating room heavy equipment over such apparatus, and need for foot comfort of persons standing in such a surgery area.

SUMMARY OF THE INVENTION

It is a major object of the invention to provide improved apparatus meeting the above needs. Basically, the improved liquid collection apparatus usable during surgery comprises a) a shallow tray defining a liquid receiving zone that is upwardly exposed for receiving liquid dropping from a surgery area, b) and a liquid collector in said zone for collecting said dropping liquid while allowing a surgeon to tread over said collector, during surgery.

In one of its forms, the liquid collector comprises a tube lying generally horizontally in said tray zone, the tube having at least one liquid inlet, and at least one suction outlet. As will be seen, the tube typically extends horizontally and n the tray liquid receiving zone, and has at least one suction inlet and one suction outlet. The tube preferably has multiple liquid inlets spaced along its length, and is flexible. Also, the tube may extend to a perimeter wall defined by the tray for communication with a suction line outside the tray.

It is another object to provide an easily handled, as for example foldable, tray structure, which may consist of flexible plastic foam, as for example closed cell polyethylene foam.

A further object is to provide a liquid collector that comprises a porous mat received in the tray to extend horizontally to allow surgeon treading on the mat, as during surgery. The mat typically extends over a liquid collection tube in the tray, as referred to. At least some liquid collecting on the mat drains through the mat, or over its edges to collect in the tray for removal, as by the tube referred to.

Yet another object is to provide a releasable holder or holders for holding the mat in position in the tray. Such holder or holders may compress hook and pile material between mat and tray surfaces; and certain of such holders may extend flatly, proximate corners defined by the mat and tray. The gap or gaps between the mat edge or edges and tray peripheral wall or walls typically has width substantially less than the surgeon's shoe or boot width, i.e. the gap is less than about 4 inches.

These and other objects and advantages of the invention, as well as the details of an illustrative embodiment, will be more fully understood from the following specification and drawings, in which:

DRAWING DESCRIPTION

FIG. 4 is an enlarged fragmentary section showing a surgeon's foot treading on the mat, and over the suction tube;

FIG. 5 is a fragmentary section showing a grate modification;

FIGS. 6a and 6b are sections showing drain tube exiting modification;

FIG. 7 is a cross-section taken through a modified drain tube;

FIG. 8 is a cross-section taken through two trays that are joined end-to-end; and FIG. 9 is a cross-section showing a non-slip upper surface of batting in the tray.

DETAILED DESCRIPTION

Figure 1:
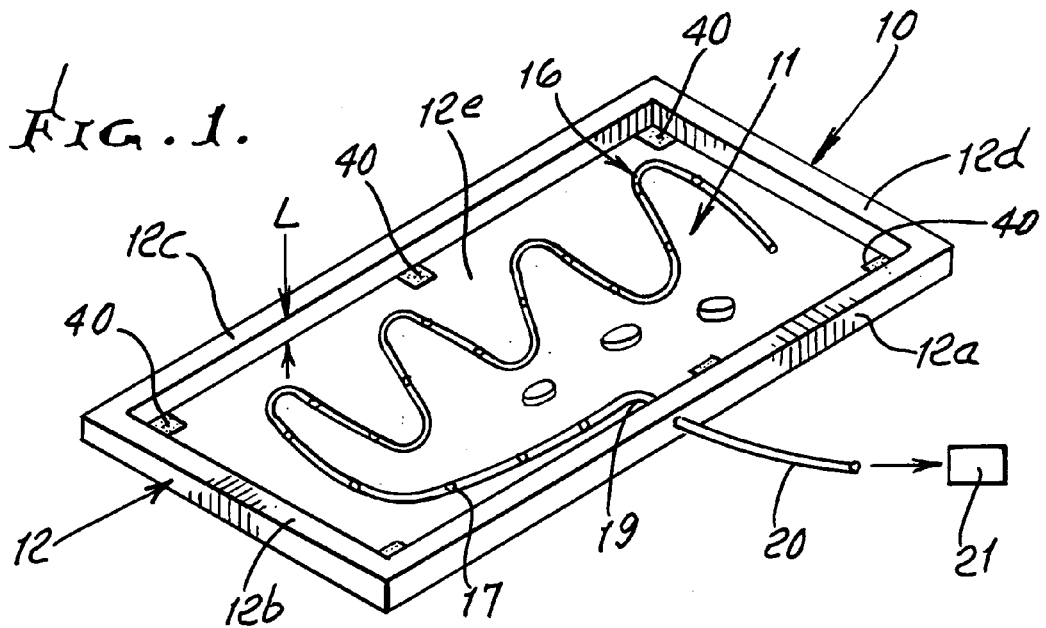
FIG. 1 is a perspective view of a preferred embodiment of collector tray apparatus embodying the invention, and suction tube in the tray.
Figure 2:
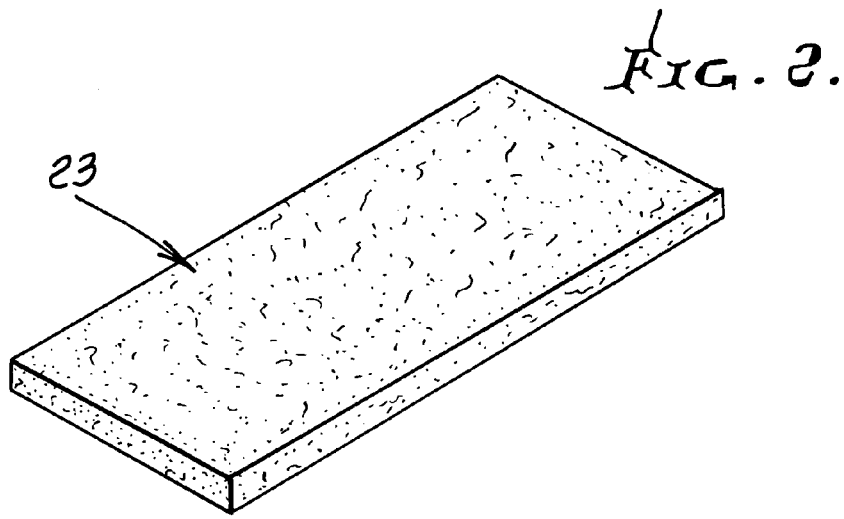
FIG. 2 is a perspective view of a mat to fit in the tray.

FIG. 1 shows a preferred shallow tray 10 defining a liquid receiving zone 11 bounded by a peripheral wall 12 defining side wall stretches 12a–12d. Shallow zone is upwardly exposed for receiving liquid dropping from a surgery area, i.e. an operating table. Such liquid typically includes water and body fluid as indicated at 13 in FIG. 3, dropping toward the tray. The tray preferably consists of lightweight flexible plastic foam, enabling easy folding for removal and disposal. Closed cell polyethylene foam is preferred. Wall stretches 12a–12d extend peripherally across the tray thin flat bottom wall 12e, and have overall height "L" above the top of bottom wall 12e less than about 1 inch. Side wall stretches may be bonded as at 15 to the bottom wall.

Also shown in FIG. 1 is a liquid collection tube 16 extending or lying generally horizontally in zone 11, as on the top surface of bottom wall 12e. The tube outer diameter is less than the height of the wall stretches, to enable suction of liquid from tray zone 11 into the tube interior via small holes or ports 17 spaced along the tube serpentine length, as shown. The tube has at least one inlet hole 17 and preferably a multiplicity of such holes or ports; and it has a suction outlet as for example at 19 proximate the wall stretch 12a. A suction line 20 outside the tray is connected in series with tube 16. Several such tubes 16 may be used. A suction source is indicated at 21.

The liquid collection apparatus preferably includes a mat 23 which is laid in the tray to cover the major area of the zone 11. Mat 23 is porous to allow drainage of liquid received on its upper surface through the mat, for collection. In this regard, the mat may consist of non-woven fibrous material such as polyester fiber. The mat functions to reduce splashing and as a treading surface, as for example is illustrated in FIG. 4 showing a surgeon's shoe or boot 26 applying downward loading on the mat upper surface at 23a, such loading being distributed for downward application to the tray bottom wall 12e. FIG. 4 also shows a portion of tube 16 below boot 26 being squeezed or deflected by the mat, the mat serving to transmit substantial loading to the wall 12e independently of transmission through tubing 16, whereby suction is maintained along the tube length. Also, the walls 12a–12d and mat are configured and sized to allow any required rolling travel of operating room equipment onto or over the walls and mat, as indicated by wheel 31 and leg 32 of such equipment above the mat, in FIG. 3, locally compressing the resiliently compressible mat structure. Mat overall height is preferably between ½ inch and 2 inches so that the mat upper surface is approximately at the same level as the upper surfaces of the wall stretches 12a–12d. One example of such known equipment is a Mayo Stand.

Figure 3:
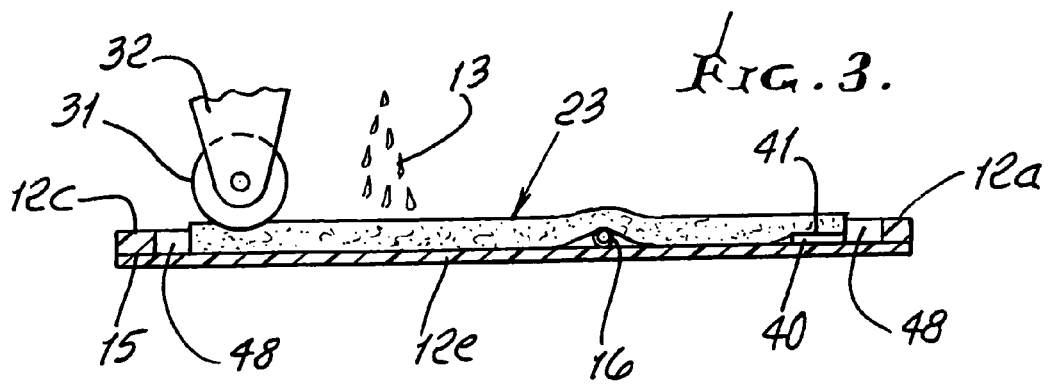
FIG. 3 is a vertical section taken through the tray, tube and mat.

FIGS. 1 and 3 also show the provision of holders to retain edges of the mat in place on the top of the mat bottom wall 12e. One example is the use of hook and pile layers (VELCRO) 40 and 41 on the top of wall 12e, and on the bottom mat proximate their corners. At the time of use, the mat is placed in the tray so that the VELCRO layers interconnect; and after use as during surgery, the mat, tray and suction tubing are disposed of. Other adhesive can be used. Note also FIG. 3 showing peripheral extent spacing 48 from walls 12a and 12c.

Further unusual advantages in construction, function and results, are as follows:

1. The tray is comfortable to stand on due to preferred foam construction. Batting provides additional cushioning. Other products do not offer this dual cushioning feature. The tray may preferably be rectangular and in one example measures approximately 44 inches×62 inches and has 1 inch high rim. It is made from vacuum formed rigid plastic sheet material and has raised round bosses within the tray to serve as a platform for standing. The height of the bosses is typically about ½ inch and the high loft non-woven batting material, or mat, covers approximately the entire tray interior to serve as both a cushion and a non-splash material. One or more drains are provided in the rim of the tray to carry the fluid away.

In another embodiment, the tray is made of cardboard that is coated by waterproof material.

In a further embodiment, the tray is made from a closed cell foam material and the rim is made by bonding, folding or rolling-up the edges. The raised platform may be eliminated or bonded in place or may be a separate insert.

In an additional embodiment, the tray is a film with a frame i.e. walls bonded to it by adhesive or heat-sealing.

In yet another embodiment, the tray has U-shape to better conform to the surgical table.

2. Liquid draining onto the batting or tray does not puddle. It flows through the batting and is suctioned away. The surgeon is not standing in a puddle of water.

3. The tray keeps the operating room floor dry. This is very important, to prevent slips and falls of persons standing on the tray or batting and other of persons.

4. When the tray edges are constituted of soft foam, they allow or facilitate easy stepping onto the tray, without tripping.

5. The batting minimizes splashing of liquid draining onto its upper surface. Other conventional products do not provide this.

6. The batting can be held in place on the tray by various different techniques or methods. These include: VELCRO (hook and pile) adhesive, heat bonding, and/or mechanical holding.

7. A grate may be placed in the tray in addition to the batting. See FIG. 5 showing a grate 50 under batting 23, in tray 10.

8. The material of the tray prevents skidding of the tray. Alternatively, non-skid patches may be placed on the underside of the tray for this purpose. Such patches appear at 51 in FIG. 5.

9. The batting may have a white or light color upper surface that permits easy visualization of collected tissue debris, and any dropped objects, such as instruments, by color contrast. One such light colored upper surface is seen at 52 in FIG. 5.

10. The tray can easily be fabricated from a flexible plastic film, a coated cardboard or rigid plastic, as by vacuum forming.

11. The drain tube 16a can exit the tray through its sidewall, or over the sidewall 12a as seen at 16aa in FIG. 6a. It could alternatively pass through a hole 53 in the center area of the tray, and then extend under the tray to the exteriors as seen in FIG. 6b.

12. The used tray is preferably flexible to be easily foldable or rollable. It can therefore be reduced in size for disposal or shipment.

13. Before disposal, lifting of one edge of the tray causes the liquid to run to the bottom edge and be easily suctioned out through drain line.

14. The tray has no sharp edges that could cause cuts during use or during disposal. This is very important because of the presence of the biological materials in and around the tray. Typically, all tray and batting materials are preferably soft.

15. The tray is preferably thermally insulating. This adds to the foot comfort of the user during use if the floor of the operating room is cold. The plastic or synthetic resinous material is thermally insulating, for this purpose, if that material is used.

16. The tray is electrically insulating. This adds a level of safety because of the presence of electrical outlets and equipment in the operating room during the surgical procedure.

17. The drain tube may have ribs on the inside diameter to prevent flow blockage. See FIG. 7, in which ribs 54 are formed to project radially from the bore 55 of a modified drain tube 16d.

18. The tray or trays may be formed as a modular system. Several trays of smaller size may be joined together to create suitable are and configuration for optimal performance. See FIG. 8 showing end wall interconnection, as via tongue and groove elements 58 and 59, of two like modular trays 12g. Batting in the trays appears at 23a. Retainer tape or plastic extrusion can be used to join multiple trays.

19. The tray can be rolled or folded in half and interlocked with other trays for compact size suitable for UPS shipment. For example, the separate trays of FIG. 8 can be folded, as at fold lines 60, for shipment.

20. The drain tube has holes of a small size so that when some of the holes are covered with liquid and others open to air, there is a residual vacuum of at least 3 inches of water at points of suction. This permits liquid to be suctioned regardless of operating room floor slope. Also, the holes are sized and spaced so that there will always be suction at the hole or holes at the remote end of the tube.

21. The batting may have a non-slip upper surface, to prevent user's foot slippage, as when the batting is wet. For example, that upper surface may be textured, irregular or roughened to provide such non-slip quality, as seen at 61 in FIG. 9. A thin disposable film 62 covers the tray.

22. The tray may consist of open cell foam, with waterproof film on top. It can then be compressed or vacuum packed to make its volume smaller for shipping. Polyurethane foam can be used, for this purpose.

23. To control the battery and make it of uniform height, (to prevent tripping hazard) a net material can be used to retain the mat and secure it to the foam tray. This also eliminates need for adhesive between battery and tray foam.

24. The hole pattern in tubing can be varied in size and location for optimum suction control. The holes can be punched, for clean edges. The tubing material (vinyl) is preferably soft to allow chairs to roll over it and to make it comfortable to stand on. The foam used for the tray allow the tubing to pass through the wall without use of sealant.

25. Other applications for the system include use on flooring in ambulances, rescue helicopters, burn units, morgues, and other medical areas.

26. The tray, mat and tubing system, when discarded or moved, holds its fluid contents, preventing spilling of fluid onto the floor.

27. Channels or guides can be provided in the mat, to retain the tubing.

28. The mat can be used for EMS, on which a patient lies while being transported. Thermal insulating properties maintain the patient warm, and help prevent hypothermia, while keeping an ambulance floor clean.

We claim:

1. Liquid collection apparatus usable during surgery, comprising, in combination:
   a) a shallow tray defining a liquid receiving zone that is upwardly exposed for receiving liquid dropping from a surgery area,
   b) and a liquid collector in said zone for collecting said dropping liquid while allowing a surgeon to tread over said collector, during surgery,
   c) the tray having flexible plastic extent that is foldable,
   d) said collector comprising a porous mat received in the tray to extend generally horizontally to allow surgeon treading on the mat, and a tube extending generally horizontally in said tray zone, the tube having at least one liquid inlet, and a suction outlet,
   e) the tray having an upstanding wall extending about said liquid receiving zone and about said mat,
   f) the mat consisting of fibrous material and in which liquid dropping toward the tray is collected, the mat overall height being between ½ inch and 2 inches,
   g) said tube extending to a perimeter wall defined by the tray, the tube having multiple liquid inlets spaced along its length, and being flexible, that perimeter wall having height less than about one inch, as measured from the top of the tray bottom wall;
   h) there being a spacing from said upstanding wall and about the mat peripheral extent for allowing liquid drainage off the mat to gain access to an inlet or inlets defined by the tube.

2. The combination of claim 1 including a suction line outside the tray, and connected in series with the tube.

3. The combination of claim 1 wherein the tray consists of flexible plastic foam.

4. The combination of claim 3 wherein said foam consists of closed cell polyethylene foam.

5. The combination of claim 3 wherein said porous mat is received in the tray to extend generally horizontally to allow surgeon treading on the mat, during surgery.

6. The combination of claim 5 wherein the tray upstanding wall extends about said mat.

7. The combination of claim 5 including a releasable holder or holders holding the mat in position in the tray.

8. The combination of claim 1 wherein said holder or holders include hook and pile material between the mat and tray.

9. The combination of claim 8 wherein certain of said holders extend flatly proximate corners defined by the mat and tray.

10. Liquid collection apparatus usable during surgery, comprising, in combination:
    a) a shallow tray defining a liquid receiving zone that is upwardly exposed for receiving liquid dropping from a surgery area,
    b) and a liquid collector in said zone for collecting said dropping liquid while allowing a surgeon to tread over said collector, during surgery,
    c) said collector comprising a porous mat received in the tray to extend generally horizontally to allow surgeon treading on the mat, during surgery.
    d) and wherein said collector also comprises a tube extending generally horizontally in said tray zone, the tube having at least one liquid inlet, and a suction outlet, and said tube located beneath the mat,
    e) the mat having peripheral extent with spacing from an upstanding wall defined by the tray, said spacing allowing liquid drainage off the mat to gain access to an inlet or inlets defined by the tube.

11. The combination of claim 10 wherein the tube extends to said upstanding wall defined by the tray.

12. The combination of claim 11 wherein the tray, mat and tube are flexible and foldable, for storage before or after use.

13. The combination of claim 11 wherein the mat consists of non-woven fibrous material and in which liquid dropping toward the tray is collected.

14. The combination of claim 10 wherein said spacing is everywhere upwardly exposed.

15. Liquid collection apparatus usable during surgery, comprising, in combination:
    a) a shallow tray defining a liquid receiving zone that is upwardly exposed for receiving liquid dropping from a surgery area,
    b) and a liquid collector in said zone for collecting said dropping liquid while allowing a surgeon to tread over said collector, during surgery,
    c) said collector comprising a porous mat received in the tray to extend generally horizontally to allow surgeon treading on the mat, during surgery,
    d) and wherein the mat has peripheral extent with spacing from an upstanding wall defined by the tray, said spacing corresponding to an outer portion of said liquid receiving zone that allows liquid removal off the mat while said zone remains upwardly exposed as aforesaid,
    e) and including at least a portion of a suctioning tube that extends in said spacing to suction liquid drainage off the edge of the mat.

16. The method of collecting liquid drainage from a surgical zone, as during surgery, that includes:
    a) providing and deploying apparatus as defined in claim 10
    b) and suctioning said liquid to remove it from the tray after collecting it in the tray,
    c) the collector allowing treading in the tray,
    d) and subsequently folding said tray, for disposal,
    e) and wherein said tray is provided to consist of lightweight flexible sheet plastic material enabling tray folding.

17. The method of claim 16 wherein said tray is provided to consist of flexible plastic foam enabling tray folding.

18. The method of claim 16 including deploying said suctioning tube in the tray and applying suction to said tube to effect said liquid suctioning.

19. The method of claim 16 wherein the tray is provided to form said perimeter wall extending about said drainage reception zone.

20. The method of claim 19 including laying the mat to extend flatly in the tray drainage reception zone, the mat configured to provide a treading upper surface, during surgery.

21. The method of collecting liquid drainage from a surgical zone, as during surgery, that includes:
    a) providing and deploying a foldable shallow tray to form a liquid drainage recapture zone upwardly exposed toward the surgical zone,
    b) providing a liquid collector in the tray for collecting said liquid drainage,
    c) and suctioning said liquid to remove it from the tray after collecting it in the tray,
    d) the collector allowing treading in the tray,
    e) and subsequently folding said tray, for disposal,
    f) and wherein said tray is provided to consist of lightweight flexible plastic foam sheet material allowing tray folding,
    g) providing a porous mat defined by said collector and laying the mat to extend flatly in the tray drainage reception zone, the mat configured to provide a treading upper surface, during surgery,
    h) the mat positioned in the tray to provide a liquid collection space between the mat edge and said upstanding wall, and positioning said suctioning tube in the tray so that at least a portion of the tube has at least one suctioning inlet located in said space.

22. The method of claim 21 including rollably traveling operating room equipment upon and over said tray and mat, during surgery.

23. The method of claim 21 including providing a thin disposable film covering the tray.

24. The method of claim 21 including providing a grate in the tray in stacked relation to the liquid collector.

25. The apparatus of claim 24 wherein the collector comprises porous batting, and the grate extends under the batting.

26. The apparatus of claim 1 including a non-skid element which is one of the following:
    i) a non-skid bottom surface of the tray,
    ii) a non-skid patch at the underside of the tray.

27. The apparatus of claim 1 wherein the mat has a white or light colored upper surface.

28. Liquid collection apparatus as defined in claim 1 wherein the tray is sufficiently flexible to be foldable with multiple folds, and/or rollable, with or without said collector.

29. The method of claim 18 including lifting an edge or edges of the tray to cause liquid in the tray to drain toward said tube in the tray, for suctioning.

30. The apparatus of claim 28 wherein the tray is free of sharp edges that could cause cuts or injury to the hand of personnel manipulating the tray as during installation, use, or disposal.

31. The apparatus of claim 1 wherein the tray consists of at least one of the following materials:
    i) thermally insulating material,
    ii) electrically insulating material.

32. Liquid collection apparatus usable during surgery, comprising, in combination:
    a) a shallow tray defining a liquid receiving zone that is upwardly exposed for receiving liquid dropping from a surgery area,
    b) and a liquid collector in said zone for collecting said dropping liquid while allowing a surgeon to tread over said collector, during surgery,
    c) and wherein said collector comprises a tube laying generally horizontally in said tray zone, the tube having at least one liquid inlet, and a suction outlet,
    d) and wherein the tube has internal, generally axially extending ribbing.

33. Liquid collection apparatus as defined in claim 1 including multiple of said trays which are interconnected to from a modular system.

34. The combination of claim 33 wherein the multiple trays are flexible and folded or rolled, for shipment.

35. Liquid collection apparatus as defined in claim 1 wherein said mat has an upper surface characterized as non-slip, with at least one of the following configurations:
    i) textured,
    ii) irregular,
    iii) roughened,
    iv) fibrous.

* * * * *